(12) United States Patent
Rössler et al.

(10) Patent No.: US 8,632,336 B2
(45) Date of Patent: Jan. 21, 2014

(54) TOOTH IMPLANT

(75) Inventors: Hans-Dieter Rössler, Kleinostheim (DE); Fabian Peters, Mannheim (DE)

(73) Assignee: Riemser Pharma GmbH (DE)

( * ) Notice: Subject to any disclaimer, the term of this patent is extended or adjusted under 35 U.S.C. 154(b) by 32 days.

(21) Appl. No.: 12/064,590

(22) PCT Filed: Aug. 18, 2006

(86) PCT No.: PCT/CH2006/000439
§ 371 (c)(1),
(2), (4) Date: Mar. 12, 2008

(87) PCT Pub. No.: WO2007/022655
PCT Pub. Date: Mar. 1, 2007

(65) Prior Publication Data
US 2008/0241792 A1    Oct. 2, 2008

(30) Foreign Application Priority Data

Aug. 22, 2005 (EP) .................................. 05405487

(51) Int. Cl.
*A61C 8/00* (2006.01)
(52) U.S. Cl.
USPC ........................................ 433/174; 433/201.1
(58) Field of Classification Search
USPC ................ 433/172–174, 201.1; 606/300–301
See application file for complete search history.

(56) References Cited

U.S. PATENT DOCUMENTS

| | | | |
|---|---|---|---|
| 4,850,870 A | 7/1989 | Lazzara et al. | 433/174 |
| 5,006,068 A | 4/1991 | Lee et al. | 433/169 |
| 5,030,095 A * | 7/1991 | Niznick | 433/173 |
| 5,106,300 A | 4/1992 | Voitik | 433/173 |
| 5,403,136 A | 4/1995 | Mathys | |
| 5,538,426 A | 7/1996 | Harding et al. | 433/172 |
| 5,549,475 A | 8/1996 | Duerr et al. | |
| 5,779,480 A * | 7/1998 | Groll et al. | 433/173 |
| 5,782,918 A * | 7/1998 | Klardie et al. | 606/60 |
| 5,816,809 A | 10/1998 | Sapkos | 433/172 |
| 5,829,977 A | 11/1998 | Rogers et al. | 433/172 |
| 5,947,736 A * | 9/1999 | Behrend | 433/214 |

(Continued)

FOREIGN PATENT DOCUMENTS

| | | |
|---|---|---|
| DE | 103 15 399 | 9/2004 |
| KR | 2007009060 | 1/2007 |

(Continued)

OTHER PUBLICATIONS

International Search Report dated Oct. 27, 2006 issued in corresponding PCT Application No. PCT/CH2006/000439.

(Continued)

*Primary Examiner* — Cris L Rodriguez
*Assistant Examiner* — Hao D Mai
(74) *Attorney, Agent, or Firm* — Ostrolenk Faber LLP

(57) ABSTRACT

The tooth implant includes a conical screw section with a multiple thread, which broadens progressively from the rounded apical end thereof, is adjoined by a multiple micro-thread with a lower pitch. Such an implant has improved primary stability and avoids the injury of anatomical structures and with the micro-thread thereof avoids too high a compression and necrosis. In one example, an abutment with a post is fixed to the implant, which post includes a groove to which various structures can be clipped.

20 Claims, 3 Drawing Sheets

(56) References Cited

U.S. PATENT DOCUMENTS

| | | | |
|---|---|---|---|
| 6,068,479 A | 5/2000 | Kwon | 433/172 |
| 6,168,436 B1 | 1/2001 | O'Brien | 433/173 |
| 6,315,562 B1 * | 11/2001 | Kumar | 433/173 |
| 6,358,050 B1 * | 3/2002 | Bergstrom et al. | 433/173 |
| 6,398,786 B1 * | 6/2002 | Sesic | 606/308 |
| 6,402,515 B1 | 6/2002 | Palti et al. | |
| 6,464,500 B1 | 10/2002 | Popovic | 433/173 |
| 6,508,650 B2 * | 1/2003 | Gittleman | 433/172 |
| 6,547,564 B1 * | 4/2003 | Hansson | 433/174 |
| 6,655,961 B2 * | 12/2003 | Cottrell | 433/173 |
| 6,672,872 B2 * | 1/2004 | Cottrell | 433/173 |
| 6,824,386 B2 | 11/2004 | Halldin et al. | 433/173 |
| 6,913,465 B2 | 7/2005 | Howlett et al. | 433/173 |
| 7,632,096 B2 | 12/2009 | Gittleman | 433/173 |
| 7,677,891 B2 * | 3/2010 | Niznick | 433/174 |
| 7,785,107 B2 | 8/2010 | Niznick | 433/713 |
| 2002/0025505 A1 | 2/2002 | Beaty et al. | |
| 2003/0082498 A1 * | 5/2003 | Halldin et al. | 433/173 |
| 2003/0124488 A1 | 7/2003 | Gittleman | 433/173 |
| 2004/0006346 A1 | 1/2004 | Holmen et al. | |
| 2004/0101808 A1 | 5/2004 | Porter et al. | |
| 2004/0219488 A1 | 11/2004 | Choi et al. | |
| 2005/0233281 A1 | 10/2005 | Gittleman | 433/173 |
| 2006/0141418 A1 | 6/2006 | Heo | 433/173 |
| 2006/0246397 A1 * | 11/2006 | Wolf | 433/173 |
| 2007/0037123 A1 | 2/2007 | Mansueto et al. | 433/173 |
| 2007/0099153 A1 | 5/2007 | Fromovich | |
| 2008/0182227 A1 | 7/2008 | Wolf et al. | 433/174 |
| 2008/0233539 A1 | 9/2008 | Rossler et al. | |

FOREIGN PATENT DOCUMENTS

| | | |
|---|---|---|
| WO | WO 02/17814 | 3/2002 |
| WO | WO 2004/073541 | 9/2004 |
| WO | WO 2004/098442 | 11/2004 |
| WO | WO 2004/103202 | 12/2004 |

OTHER PUBLICATIONS

International Preliminary Report on Patentability dated Mar. 4, 2008 in PCT/CH2006/000439.

International Search Report in English dated Feb. 19, 2007, issued in corresponding PCT Application No. PCT/CH06/000438.

International Preliminary Examination Report dated Mar. 4, 2008 for PCT/CH2006/000438.

Office Action issued in co-pending U.S. Appl. No. 12/064,555 dated Aug. 17, 2011.

Office Action issued in co-pending U.S. Appl. No. 12/064,555 dated Feb. 14, 2011.

Office Action issued in co-pending U.S. Appl. No. 12/064,555 dated Aug. 24, 2010.

Office Action issued in co-pending U.S. Appl. No. 12/064,555 dated Mar. 19, 2010.

* cited by examiner

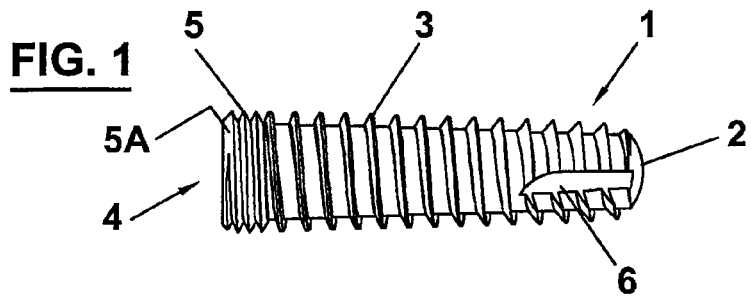
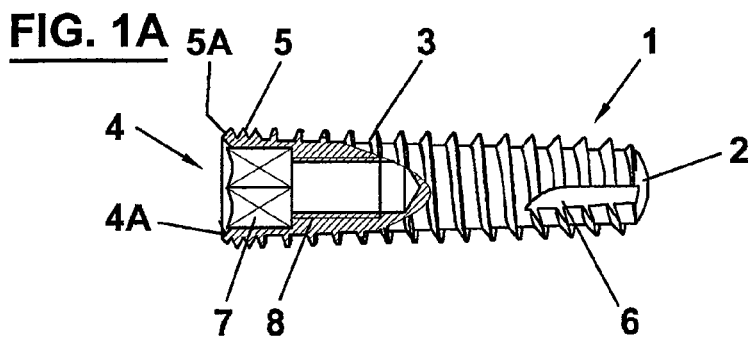
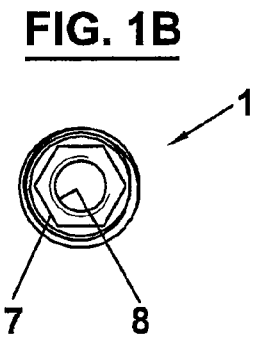
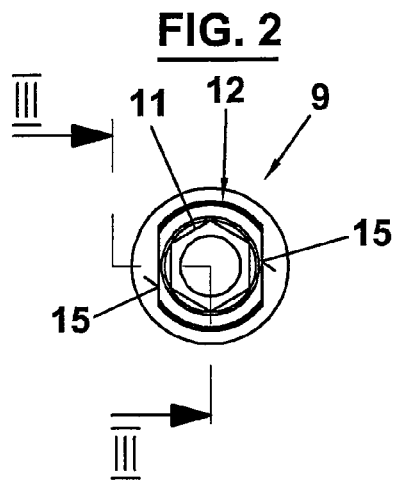
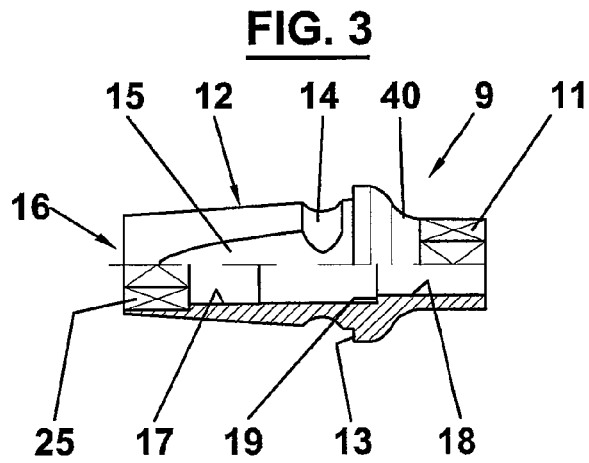
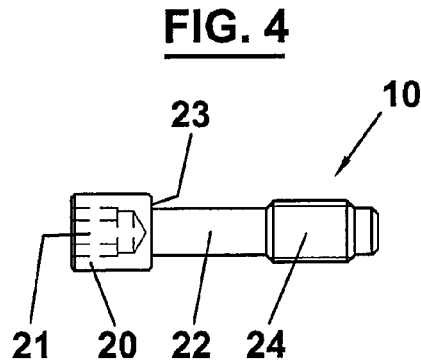
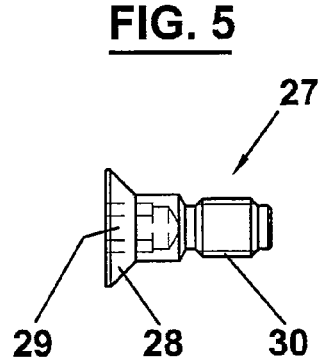

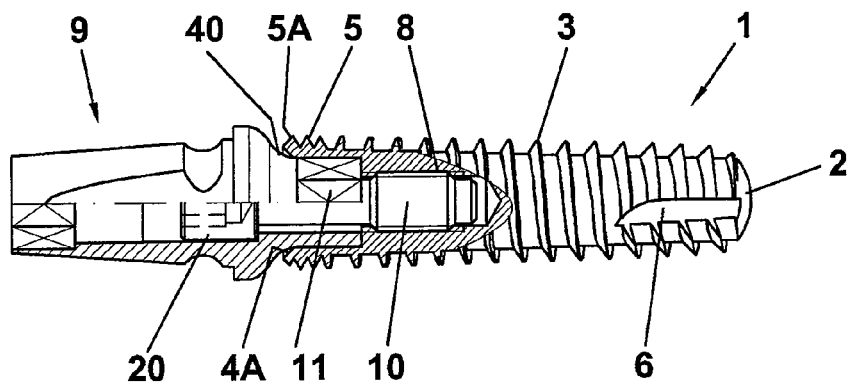
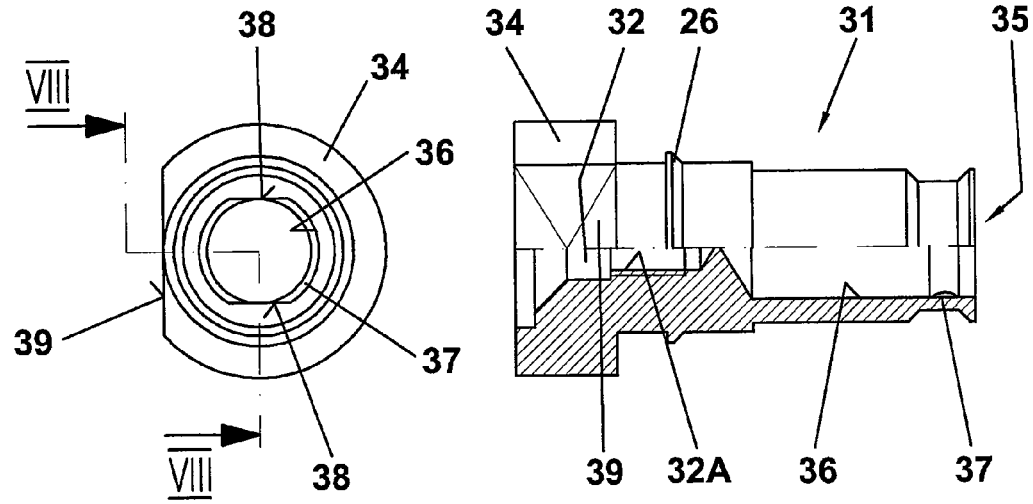
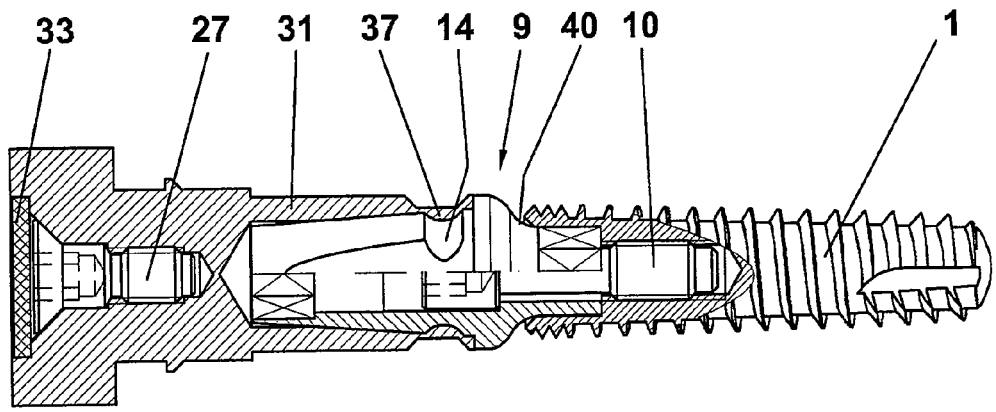

TOOTH IMPLANT

CROSS REFERENCE TO RELATED APPLICATION

The present application is a 35 U.S.C. §§371 national phase conversion of PCT/CH2006/000439, filed Aug. 18, 2006, which claims priority of European Patent Application No. 05405487.9 filed Aug. 22, 2005, the disclosure of which has been incorporated herein by reference. The PCT International Application was published in the German language.

BACKGROUND OF THE INVENTION

The present invention relates to a tooth implant, having a conical fastening portion with a thread which becomes progressively wider from the rounded apical end. A tooth implant of that kind is known from U.S. Pat. No. 6,402,515. The single, progressive thread disclosed therein is provided to improve adhesion of the tooth implant in the bone.

There is known from US 2004/101808 A1 an implant system having a double anti-rotational structure between the implant and the abutment. In that case, the implant has a conical shape with rounded apical end.

US 2004/219488 A1 discloses what is referred to therein as a micro-thread which follows on from a two-start thread. That micro-thread contains a number of small helical grooves.

There is known from WO 2004/098442 a screw-in tooth implant in which groove-like recesses are stamped into a relatively coarse thread, which recesses extend in the direction of the turns of the thread and produce there a so-called micro-thread in order to increase the area of contact between the tooth implant and bone tissue. The threaded pin itself is substantially cylindrical and the thread is not progressive.

U.S. Pat. No. 5,403,136 discloses a tooth implant with screw thread, which towards the cervical end has a thread with a decreasing pitch. The main part of the pin is cylindrical and is plane at the apical end.

US-A1-2004/0006346 discloses a tooth implant pin that is substantially cylindrical and has a plane apical end. The pin has two different threads, a relatively coarse single thread and then a so-called micro-thread which in this case is in the form of a triple thread.

WO 2004/103202 discloses, like the first-mentioned U.S. patent, a conical tooth implant with a progressive thread.

SUMMARY OF THE INVENTION

Proceeding from that prior art, it is a first object of the present invention to create a tooth implant that, in a combination of various features, provides for minimally invasive insertion, tissue conservation and good primary stability together with good bone adhesion. That object is attained with the tooth implant according to patent claim 1.

It is a further object of the invention to provide a tooth implant that is simple and inexpensive to produce and that includes, in addition to a good anchoring structure, an abutment that simplifies subsequent operations. That object is attained with the tooth implant according to patent claim 5.

Further advantages, such as, for example, good handling, are defined in the dependent claims.

BRIEF DESCRIPTION OF THE DRAWINGS

The invention will be described in detail hereinafter with reference to drawings of illustrative embodiments.

FIG. 1 shows a tooth implant according to the invention in plan view,

FIG. 1B is a view from the left of FIG. 1,

FIG. 1A shows a partial section of FIG. 1,

FIG. 2 shows an abutment for the tooth implant of FIG. 1, viewed from the front, FIG. 3 shows the abutment in accordance with the section III-III in FIG. 2, FIG. 4 shows a retaining screw, FIG. 5 shows a closure screw, FIG. 6 shows an abutment screwed to the tooth implant, FIG. 7 shows a snap-on cap, viewed from the front, FIG. 8 shows the snap-on cap in accordance with the line VIII-VIII in FIG. 7, FIG. 9 shows a tooth implant ready for despatch, assembled with an abutment and having a snap-on cap.

DETAILED DESCRIPTION

Figure 10:
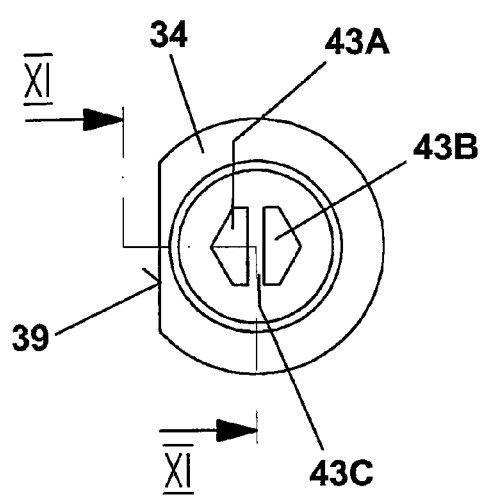
FIG. 10 shows an implementation variant for implementation according to FIG. 7, with a transfer part, viewed from the front.

FIGS. 1, 1A and 1B show a tooth implant 1, preferably made of pure titanium, having the rounded apical end 2, the progressive multiple thread 3, in this illustrative embodiment a two-start, self-tapping thread, which becomes wider from the apical end to the other, cervical end 4 and which is adjoined by a micro-thread 5, similarly a multiple thread, for example a three-start thread.

The micro-thread 5 is adjoined towards the cervical end 4 by a tapered portion 5A and the implant has an inwardly oriented chamfer 4A. Both measures make better bone adhesion possible and thus prevent bone resorption and promote growth of connective tissue at the cervical end of the implant. When an abutment having an outwardly curved shoulder is used, the effective biological width is increased with the tapered portion and the chamfer.

The rounded apical end largely prevents injury to anatomical structures such as the floor of the sinus, the floor of the nose, the mandibular nerve or the mucosa when the tooth implant is being screwed in.

The tooth implant 1 further has a conical shape which tapers towards the apical end 2, which increases the primary stability in comparison with a cylindrical tooth implant shape when being screwed into a straight cavity, and results in perfect adaptation in the cervical region.

The progressive multiple thread considerably improves the primary stability. A high mechanical primary stability is the most important prerequisite for immediate and early loading of the tooth implant. By virtue of the progressive thread, micro-movements of the inserted tooth implant are largely prevented and, as a result, incorporation of the implant and osseointegration are promoted.

In the cervical region, the progressive thread becomes a multiple micro-thread in order to avoid excessively high compression and necrosis in the corticalis. The tooth implant further has in the apical region cutting channels 6, for example two, which also serve as relief channels for the bone chips.

It will be apparent from FIGS. 1A and 1B that the tooth implant has at the cervical end a hexagon socket 7 adjoined by a bore 8 with thread.

FIGS. 2 and 3 show an abutment 9 which may be fastened to the tooth implant by means of a retaining screw 10, see FIG. 4. The abutment is preferably also made of pure titanium and has a connecting portion 11 constructed as a hexagonal element which fits into the hexagon socket 7 of the tooth implant. That hexagonal element 11 is adjoined by a multifunctional post 12 which, starting at the connecting portion, has a platform 13 and tapers from there towards the end. Close to the platform 13, there is a circumferentially extending groove 14, and two opposing flat portions 15 are disposed longitudinally of the post.

The groove in the cervical region of the post makes it possible to use a snap-on technique for various parts, which is simple to manage, very precise and time-saving. That applies especially to the transfer, to the fastening of the temporary crown or to impression-taking with a multifunctional snap-on cap, see FIGS. 7 to 9. In addition, the groove serves to enable optimum distribution of the fastening cement when the final restoration is being inserted.

As is apparent from FIG. 2, the abutment is constructed as a sleeve and has a continuous bore with two different diameters. Viewed from the cervical end 16, the diameter of the bore 17 is greater than that of the adjoining bore 18, thereby forming a shoulder 19 on which the head of the retaining screw is supported. Disposed at the cervical end there is a hexagon socket 25 by means of which the implant together with the abutment is screwed into the bone by a hexagon screwdriver.

The retaining screw 10 serves to fasten the abutment to the tooth implant and is constructed accordingly. In FIG. 4, described from left to right, the retaining screw comprises a head 20 with a hexagon socket 21, a cylindrical portion 22 and a shoulder 23 therebetween and, adjoining the cylindrical portion, a thread 24 corresponding to the bore with thread 8 in the tooth implant.

From FIG. 6, a combination of the tooth implant with the abutment, it will be apparent that the retaining screw 10 extends through the abutment and can be screwed into the tooth implant with a hexagon screwdriver. The shoulder 23 of the retaining screw 10 is supported during that operation on the shoulder 19 of the abutment, with the result that as the retaining screw is screwed in, the abutment and the tooth implant are pulled together and secured.

As will be apparent from the combination shown in FIG. 6, the abutment post 12 has a smaller diameter than that of the tooth implant in order to assist the attachment of soft and hard tissue and, in the long term, prevent bone resorption risk of infection. The multifunctional post 12 is to be used as standard for all tooth implants of this system, even in the case of different diameters, and serves
 a) as a transfer post from the double sterile packaging into the predrilled cavity,
 b) for screwing into the predrilled cavity,
 c) as a temporary post and
 d) as the final post.

The two flat portions 15 of the post serve on the one hand to cement the crown in a manner securing it against rotation and to obtain correct axial alignment. This makes precise transfer possible.

The posts are preferably coded, for example by giving them a bicolour marking, to avoid confusion. The flat surfaces may in that case be left untreated or uncoloured.

To obtain a stable press-fit between abutment and tooth implant, the hexagonal element 11 and the hexagon socket 7 of the tooth implant have a conicity of from 0.5° to 7°. This also makes exact transfer possible, since it is not possible for wobbling to occur, as is unavoidable in the case of straight surfaces owing to the necessary tolerance.

The biological width, the connective tissue covering at the cervical implant end, is according to Tarnow and other authors from 1.5 to 3.5 mm. The previously prepared shoulder 40 on the fastening portion of the abutment of approximately from 1.7 to 2.1 mm, preferably 1.9 mm, above the end of the tooth implant takes that biological width of the soft tissue into account, which provides considerable advantages for long-term success from an aesthetic and a functional point of view. That effect is assisted by the tapered portion 5A and the chamfer 4A at the cervical end of the implant.

The described abutment having the post with a circumferentially extending groove for a snap-on technique is advantageous not only in respect of the implant 1 described in the introduction but also in respect of other types of implant, in which case, however, the connecting portion has to be of an appropriate form and may have, instead of a hexagonal element, other coupling means.

If the tooth implant is to grow in without the abutment, it is essential to seal its opening 7 and 8. There is used for that purpose the closure screw 27 of FIG. 5, which has a countersunk head 28 with a hexagon socket 29 and a thread 30 that fits into the thread 8 of the tooth implant.

In the packaging ready for despatch shown in FIG. 9, that closure screw is screwed into a corresponding recess 32 at the rear portion of a snap-on cap 31 and is secured by means of a cover 33.

The multifunctional snap-on cap 31 is made from a burn-out plastics material and, as its name reveals, it is able to perform various functions:
 a) it may serve as an introduction aid for transfer from the sterile packaging into the predrilled cavity and for screwing-in of one to two turns.
 b) it may serve as a base for the temporary crown which can be fitted exactly. Fastening of the crown is effected by means of the described snap-on technique and temporary cement.
 c) it may serve as an impression cap in conjunction with prefabricated laboratory tooth implants to obtain exact transfer. The shape of the snap-on cap is matched to the post of the abutment.
 d) it may serve as a pre-modelled crown base for the dental technician and as a base for the final restoration after the technician has milled away the receiving ring 34.

The snap-on cap altogether makes possible an economical workflow in the collaboration between dentist and dental technician, saving time and affording high precision.

The snap-on cap has at its apical end 35 a bore 36 with a neck 37 which corresponds to the groove 14 of the abutment post. Accordingly, the snap-on cap may be snapped onto the abutment post in order to be securely fixed there. In addition, at its periphery it has a bead 26.

So that the snap-on cap may be used as a screwing-in aid it must be held in a manner securing it against rotation relative to the abutment post. That is achieved by means of the snap-on cap having in the inner bore 36 two opposing flat surfaces 38 which cooperate with the two flat portions 15 of the abutment post.

The closure screw 27 is inserted in a receiving ring 34 of the cap, which ring has a flat portion 39 which serves to secure a crown.

Figure 11:
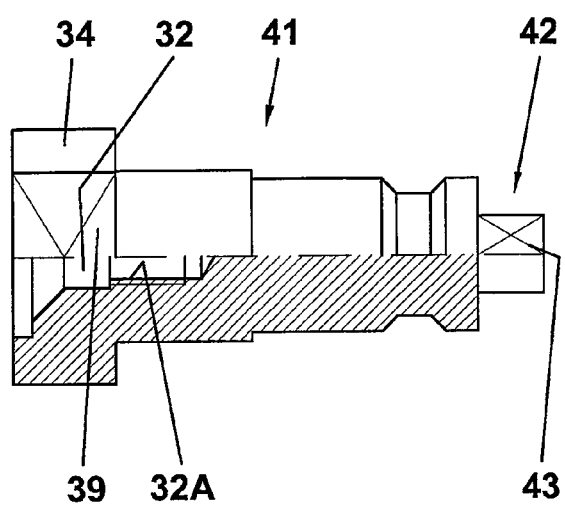
FIG. 11 shows the transfer part in accordance with the line XI-XI in FIG. 10.
Figure 12:
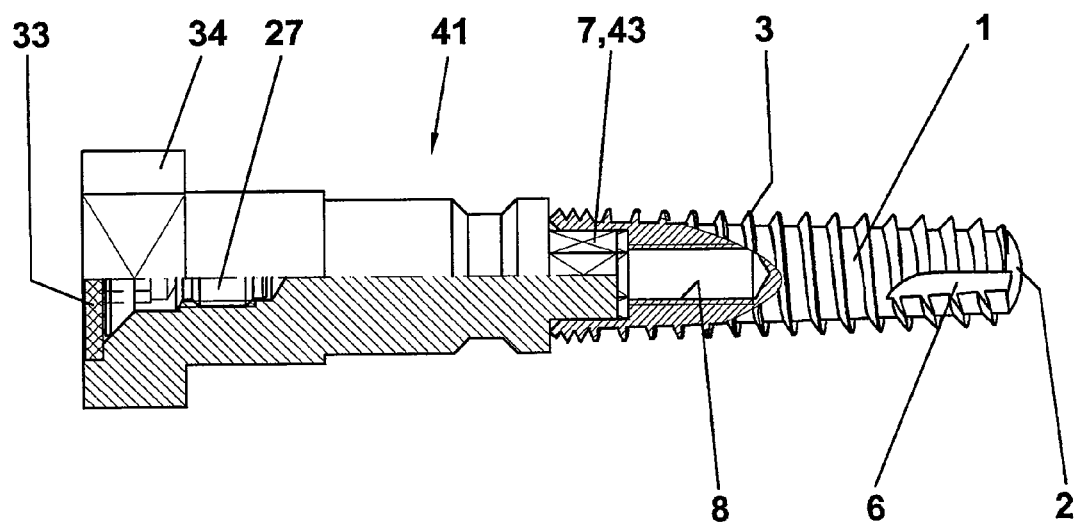
FIG. 12 shows a tooth implant ready for despatch, with a transfer part.

FIGS. 10 to 12 show a transfer part 41 which may be directly connected to the implant 1 and not to the abutment as in the previous example. For that purpose, the transfer part has at its apical end 42 a hexagonal element 43 which consists of two halves 43A and 43B, the halves being separated by a gap 43C, as a result of which they are resilient. That hexagonal element corresponds to the hexagon socket 7 of the implant and may similarly have a conicity of from 0.5° to 7°.

The remaining configurations and features as well as advantages and possible applications of the transfer part 41 correspond to those of the snap-on cap 31 shown in FIGS. 7 to 9. That applies also to the receiving of a closure screw 27. In FIG. 12, the implant with the transfer part is shown partly in section.

The invention claimed is:

1. A dental implant system comprising a tooth implant, an abutment, a snap-on cap and a transfer part, wherein the tooth implant includes:
   an apical end, which is rounded;
   an opposite cervical end;
   an inwardly oriented chamfer at the cervical end;
   a conical screw portion located between the apical and cervical ends, the conical screw portion having a progressive multiple thread, and
   a micro-thread portion adjoining the conical screw portion and having a multiple micro-thread, wherein the conical screw portion and the micro-thread portion extend between the apical end and the cervical end, the conical screw portion begins at the apical end and extends to the micro-thread portion, and the micro-thread portion begins at the conical screw portion and extends to the cervical end;
   a hexagon socket at the inwardly oriented chamfer spaced from the cervical end, wherein the hexagon socket is tapered to define a conicity, which is in the range from 0.5° to 7°,
   wherein the abutment comprises a connecting portion at a first end of the abutment that fits into the hexagon socket of the tooth implant and a post at an opposite end of the abutment with a groove located in the post,
   wherein the transfer part includes a connecting portion which is a hexagonal element and is configured to be plugged into the hexagon socket of the tooth implant when in absence of the abutment,
   wherein the snap-on cap is a multifunctional snap-on cap having a cross-section with a circular outer surface, the multifunctional snap-on cap having, at its apical end, a bore, which includes an internal neck, which is configured to be snapped into said groove in the post of the abutment, the bore having a first internal surface, which is round and tapered, and a second internal surface, which is flat, the second internal surface of the bore extending along at least a portion of the length of the first internal surface of the bore, and wherein, when the internal neck is snapped into the groove, the first internal surface of the bore is opposed to a first outer surface of the post and the second internal surface of the bore is opposed to a second outer surface of the post, said first outer surface being round and said second outer surface being flat, and
   wherein the snap-on cap is configured for engaging the abutment and the transfer part is configured for engaging the implant in the absence of the abutment.

2. The system according to claim 1 wherein the tooth implant extends in an axial direction and the multiple micro-thread is adjoined towards the cervical end by a tapered portion oriented towards the axial direction.

3. The system according to claim 1, wherein the abutment is a sleeve configured to be fastened to the cervical end of the tooth implant by means of a retaining screw.

4. The system according to claim 3, further comprising a retaining screw for fastening the abutment to the cervical end of the tooth implant, the retaining screw having a thread, and wherein the tooth implant has a bore with a thread in the bore at the cervical end, the thread of the bore is configured to cooperate with the thread of the retaining screw.

5. The system according to claim 1, wherein the connecting portion of the abutment is located at the apical end of the abutment, and is constructed as a hexagonal element having a conicity of 0.5° to 7° along the length thereof.

6. The system according to claim 5, wherein the hexagonal element of the abutment is resilient and is comprised of two halves with a gap arranged therebetween.

7. The system according to claim 5, wherein the connecting portion and the post of the abutment are made in one piece and the abutment is constructed as a sleeve.

8. The system according to claim 5, wherein the abutment comprises a shoulder arranged between the hexagonal element and the groove.

9. The system according to claim 8, wherein said shoulder includes a curved surface that is located between the connecting portion and the post.

10. The system according to claim 5, wherein the post of the abutment has at its cervical end a hexagonal socket.

11. The system according to claim 1, wherein the abutment includes an outwardly curved portion, which adjoins the connecting portion.

12. The system according to claim 1, wherein the post has a smaller diameter than a diameter of the tooth implant.

13. The system according to claim 1, wherein the post has flat portions disposed longitudinally on the post.

14. The system according to claim 1, wherein the snap-on cap has a cervical end that includes a closable bore for receiving a closure screw for the tooth implant.

15. The system according to claim 14, wherein the closable bore has a thread.

16. The system according to claim 1, wherein the multiple micro-thread of the multiple micro-thread portion have a smaller pitch than a pitch of the threads of the multiple thread portion.

17. The system according to claim 1, wherein, the transfer part has a cervical end that includes a closable bore for receiving a closure screw for the tooth implant.

18. The system according to claim 1, wherein the abutment comprises a shoulder arranged between the connecting portion and the groove, and wherein the snap-on cap includes at its apical end an edge which is configured such that it is adjacent to the shoulder of the abutment when the internal neck is snapped into the groove.

19. The system according to claim 1, wherein said bore of the snap-on cap has a third internal surface, which is flat, and which, when the internal neck is snapped into the groove, is opposed to a flat third outer surface of the post of the abutment.

20. The system according to claim 19, wherein the second internal surface of the bore and the third internal surface of the bore are arranged substantially in opposition to one another.

* * * * *

UNITED STATES PATENT AND TRADEMARK OFFICE
CERTIFICATE OF CORRECTION

PATENT NO.      : 8,632,336 B2
APPLICATION NO. : 12/064590
DATED           : January 21, 2014
INVENTOR(S)     : Rössler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 102 days.

Signed and Sealed this
Twenty-second Day of September, 2015

Michelle K. Lee
*Director of the United States Patent and Trademark Office*